United States Patent
Ogawa et al.

(10) Patent No.: US 9,844,633 B2
(45) Date of Patent: Dec. 19, 2017

(54) SYRINGE

(71) Applicant: TAISEI KAKO CO., LTD., Osaka (JP)

(72) Inventors: Yukihiro Ogawa, Osaka (JP); Yuji Tanaka, Kanagawa (JP)

(73) Assignee: Taisei Kako Co., Ltd., Osaka (JP)

( * ) Notice: Subject to any disclaimer, the term of this patent is extended or adjusted under 35 U.S.C. 154(b) by 109 days.

(21) Appl. No.: 14/785,597

(22) PCT Filed: Apr. 22, 2014

(86) PCT No.: PCT/JP2014/061221
§ 371 (c)(1),
(2) Date: Oct. 19, 2015

(87) PCT Pub. No.: WO2014/175237
PCT Pub. Date: Oct. 30, 2014

(65) Prior Publication Data
US 2016/0067421 A1    Mar. 10, 2016

(30) Foreign Application Priority Data
Apr. 23, 2013    (JP) ................................. 2013-090014

(51) Int. Cl.
*A61M 5/32*    (2006.01)
*A61M 5/28*    (2006.01)
(Continued)

(52) U.S. Cl.
CPC .......... *A61M 5/3234* (2013.01); *A61M 5/283* (2013.01); *A61M 5/31571* (2013.01);
(Continued)

(58) Field of Classification Search
CPC ............ A61M 5/3202; A61M 5/31571; A61M 5/3234; A61M 5/326; A61M 5/3271;
(Continued)

(56) References Cited

U.S. PATENT DOCUMENTS 4,994,045 A *   2/1991   Ranford .............. A61M 5/3271
                                                                 604/198
5,169,392 A *   12/1992   Ranford .............. A61M 5/3271
                                                                 128/919
(Continued)

FOREIGN PATENT DOCUMENTS

EP         2578257 A1    4/2013
JP      2003164524 A    6/2003
(Continued)

OTHER PUBLICATIONS

The "International Search Report" dated Aug. 5, 2014 for the International Application No. PCT/JP2014/061221 of which the above-captioned instant U.S. patent application is a U.S. National Phase application.

*Primary Examiner* — Andrew Gilbert
*Assistant Examiner* — Hong-Van Trinh
(74) *Attorney, Agent, or Firm* — Wood, Phillips, Katz, Clark & Mortimer

(57) ABSTRACT

It is an object of the present invention to provide a syringe which is capable of preventing an accident such that a patient inadvertently sticks her/his hand with an injection needle when improperly performing a needle retracting operation. A sleeve (10) is fitted around a syringe barrel (2) so as to be axially movable from an administration position such that the injection needle (5) projects to a distill side to an accommodation position such that the injection needle (5) is accommodated. A coil spring (16) for biasing the sleeve (10) toward the accommodation position is provided between the sleeve (10) and the syringe barrel (2), and is held in a compressed state in a spring holder (17). The spring holder (17) is disposed in association with the syringe barrel (2) so as to release the coil spring by further pushing the syringe barrel (2) to the distal side after completion of the administration of a liquid drug. The sleeve (10) is axially
(Continued)

engaged with the syringe barrel (2) so as to be locked at the accommodation position when being moved to the accommodation position by a biasing force of the coil spring (16).

3 Claims, 19 Drawing Sheets

(51) Int. Cl.
    *A61M 5/315*     (2006.01)
    *A61M 5/31*     (2006.01)

(52) U.S. Cl.
    CPC .......... *A61M 5/3202* (2013.01); *A61M 5/326* (2013.01); *A61M 5/3287* (2013.01); *A61M 5/3271* (2013.01); *A61M 2005/3139* (2013.01); *A61M 2005/3241* (2013.01); *A61M 2005/3247* (2013.01); *A61M 2005/3254* (2013.01)

(58) Field of Classification Search
    CPC .......... A61M 5/321; A61M 2005/3139; A61M 2005/3241; A61M 2005/3247; A61M 2005/3254; A61M 2005/3261; A61M 2005/3235
    USPC ........................................................ 604/194
See application file for complete search history.

(56) References Cited

U.S. PATENT DOCUMENTS

| | | | | |
|---|---|---|---|---|
| 7,338,469 | B2* | 3/2008 | Barker | A61M 5/2429 604/110 |
| 2009/0299295 | A1* | 12/2009 | Rubinstein | A61M 5/326 604/198 |
| 2013/0281939 | A1* | 10/2013 | Roberts | A61M 5/326 604/198 |
| 2014/0309594 | A1* | 10/2014 | Suzuki | A61M 5/28 604/198 |

FOREIGN PATENT DOCUMENTS

| | | | | |
|---|---|---|---|---|
| JP | 2003534105 A | 11/2003 | | |
| JP | 2013094315 A | * 5/2013 | | A61M 5/28 |
| WO | 0191837 A1 | 12/2001 | | |
| WO | WO 2012093072 A1 | * 7/2012 | | A61M 5/326 |

* cited by examiner

SYRINGE

TECHNICAL FIELD

The present invention relates to a syringe.

BACKGROUND ART

PTL1 discloses a disposable spine which is capable of accommodating an injection needle in a main body thereof before and after use in order to prevent inadvertent injury with the injection, needle when a patient uses the syringe to administer a biomedical anti-cancer drug or anti-rheumatic drug to herself/himself at home.

CITATION LIST

Patent Literature

PTL1: JP-2013-519-A

In the prior-art syringe, the injection needle is accommodated within a sleeve (first holder member) and a plunger (second holder member) during storage before use. In use, the sleeve and the plunger are brought into an axially contracted state, whereby a distal portion of the injection needle projects outside from a distal portion of the first holder member. In this state, a syringe barrel (vial) is pushed with respect to the sleeve to administer a liquid drug. After completion of the administration, the sleeve and the plunger are brought into an axially extended state, whereby the injection needle is retracted within the sleeve and the plunger. The sleeve and the plunger are thereafter rotated relative to each other to be locked with respect to each other. Thus, the injection needle is prevented from projecting outside again for safe disposal of the syringe.

SUMMARY OF INVENTION

Technical Problem

With the prior art syringe, however, the needle retracting operation is manually performed after the completion of the administration. Hence, there is a possibility that the patient improperly performs the needle retracting operation to inadvertently stick her/his hand or the like with the injection needle, for example, when re-holding the syringe for the locking. Therefore, it is desirable to provide a mechanism for automatically retracting the injection needle after the administration.

WO01/32255 (JP-2003-512904-A) discloses a syringe of another type for solving the aforementioned problem. This syringe includes a needle guard which conceals the injection needle, and is configured so that the injection needle is moved out and in by pressing the needle guard against a patient's skin. In order to prevent the injection needle from projecting again, a lock member is provided which locks the needle guard at a retracted position after the first needle guard moving operation.

However, the syringe disclosed in PTL1 does not include the needle guard which is pressed against the patient's skin to be thereby moved out and in. Therefore, it is necessary to provide a mechanism for automatically retracting and locking the injection needle in response to the further pressing of the syringe barrel after the administration.

Solution to Problem

To solve the aforementioned problems, the present invention has the following technical aspects:

A syringe according to the present invention includes: a syringe barrel having an inside space to be filled with a liquid drug; a gasket fitted in the syringe barrel for sealing the liquid drug; a plunger attached to the gasket; an injection needle attached to the syringe barrel or the plunger and having a proximal portion to be brought into communication with the inside space at least when the liquid drug is to be administered; a sleeve axially movable with respect to the injection needle between an administration position such that the injection needle projects from a distal end of the sleeve and an accommodation position such that the injection needle is accommodated in the sleeve, and including a finger hook flange provided on an axially middle portion thereof; a coil spring provided between the sleeve and the syringe barrel for biasing the sleeve toward the accommodation position; and a spring holder which holds the coil spring in a compressed state. The syringe barrel may have an opening provided at a distal end or a proximal end thereof. Where the opening is directed to a distal side, the syringe can be configured so that the injection needle is held by the plunger and the proximal portion of the injection needle extends through the gasket. Where the opening of the syringe barrel is directed to a proximal side, the syringe barrel may have a nozzle provided at the distal end thereof, and the injection needle may be attached to the nozzle.

Further, one member selected from the syringe barrel and the plunger is axially engaged with the sleeve at the administration position when the liquid drug is to be administered, and the other member projects from the sleeve to the proximal side. By pushing the other member to the distal side with respect to the sleeve, the volume of the inside space is reduced so that the liquid drug flows out through the injection needle for the administration thereof. The one member is merely required to be axially engaged with the sleeve for prevention of the movement thereof to the distal aide with respect to the sleeve, and the one member may be movable to the proximal side with respect to the sleeve.

The spring bolder is connected to the other member so that the coil spring is released by further pushing the other member to the distal side after completion of the administration of the liquid drug. Various specific embodiments of the spring holder are conceivable. According to one embodiment, for example, the spring holder may be configured so as to receive a pushing force directly from the distal end of the syringe barrel to be broken to release the coil spring when the syringe barrel is strongly pushed with respect to the sleeve. According to another embodiment, the spring holder may be configured so as to receive a pushing force via the gasket and the plunger when the syringe barrel is strongly pushed with respect to the sleeve after the completion of the administration. According to further another embodiment, the spring holder may be configured so as to unlock a lock mechanism to release the coil spring, rather than to be broken by the pushing force. In any case, the spring holder is configured so as to release the coil spring when a pushing force greater than that applied to the syringe barrel and the plunger for the administration of the liquid drug is applied or when the syringe barrel and the plunger are pushed beyond an operation range thereof defined for the administration of the liquid drug (i.e., when the gasket is brought into intimate contact with the bottom of the syringe barrel and, in this state, further pushed).

Further, the sleeve is axially engaged with the syringe barrel so as to be locked at the accommodation position when the sleeve is moved to the accommodation position by the biasing force of the coil spring. The sleeve and the syringe barrel may be engaged with each other in various ways. A resilient engagement piece provided on the sleeve may be engaged directly with the syringe barrel, or the sleeve may be engaged indirectly with the syringe barrel via other component such as the plunger or the spring holder. An engagement mechanism for preventing the movement of the sleeve to the distal side and an engagement mechanism for preventing the movement of the sleeve to the proximal side may be provided at different positions in different ways. For example, the movement of the sleeve to the proximal side may be prevented by engagement of the sleeve with the syringe barrel, and the movement of the sleeve to the distal side may be prevented by engagement of the sleeve with the injection needle or the plunger.

Before the administration of the liquid drug with the use of the inventive syringe, a distal portion of the injection needle is allowed to project from the distal end of the sleeve and, in this state, a user can stick the injection needle into an accurate injection site while visually observing the injection needle. When the other member is strongly pushed with user's fingers hooked on the finger hook flange and the other member after the administration of the liquid drug, the coil spring is released from the spring holder to be brought out of the compressively held state, and the sleeve is moved to and locked at the accommodation position by the biasing force of the coil spring. This locking operation can be safely performed without the need for re-holding the syringe.

In the inventive syringe, the sleeve may include a cylindrical main body including the finger hook flange, and a safety cover attached to a distal portion of the main body. The safety cover may be engaged with the main body so as to be axially movable with respect to the main body between as compression position and an extension position axially spaced from each other. The spring holder may include a ring portion provided in opposed relation to the syringe barrel or a distal end of the plunger, and a look portion to be locked to the safety cover. The lock portion is connected to the ring portion via a connection portion which is easily breakable. The coil spring is held in a compressed state between the safety cover and the ring portion. The main body includes a first engagement recess and a second engagement recess provided in axially spaced relation in an inner surface thereof, the first engagement recess corresponding to the administration position, the second engagement recess corresponding to the accommodation position. The ring portion has a resilient engagement piece provided on an outer periphery thereof so as to be axially engaged with the first engagement recess of the main body to lock the safety cover at the compression position. The resilient engagement piece is resiliently deformable radially inward so as to permit the movement of the ring portion to the proximal side with respect to the main body. When the other member is further pushed to the distal side with respect to the sleeve main body after the administration of the liquid drug, the connection portion is broken by the pushing force to release the coil spring. The ring portion is moved to the proximal aide with respect to the main body by the biasing force of the coil spring, and the resilient engagement piece is axially engaged with the second engagement recess. Thus, the sleeve and the syringe barrel can be axially engaged with each other via the ring portion so as to prevent the movement of the sleeve toward the administration position.

With this arrangement, the coil spring can be held in the compressed state by the spring holder having the ring portion and, at the same time, the sleeve can be locked at the accommodation position after the administration. This arrangement reduces the number of components, and simplifies the mechanisms.

Preferably, the syringe barrel has the opening at its distal end, and the gasket is attached to a proximal end of the plunger. The plunger projects to the distal side from the distal end opening of the syringe barrel, and the injection needle is held by the plunger. During the administration of the liquid drug, the plunger is axially engaged with the sleeve at this administration position, and the syringe barrel projects to the proximal side from the sleeve.

More preferably, as shown in the prior art disclosed in PTL1, the sleeve is rotatably attached to the syringe barrel. The injection needle may be a double ended needle which includes a cylindrical needle base and needle portions provided at axially opposite ends of the needle base. The sleeve includes a first holding portion to be fitted around the needle base from the distal side, and the plunger includes a second holding portion to be fitted around the needle base from the proximal side. The first and second holding positions each include at least two columnar portions which hold the needle base in contact with an outer peripheral surface of the needle base. With proximal ends of the columnar portions a the first holding portion axially spaced from distal ends of the columnar portions of the second holding portion, the sleeve and the plunger may be rotatable relative to each other. With the proximal ends of the columnar portions of the first holding portion axially opposed to the distal ends of the columnar portions of the second holding portion, the total length of the first and second holding portions may be set greater than the length of the injection needle. In this case, the injection needle can be accommodated inside the first and second holding portions during the storage before the administration. At the same time, it is possible to prevent the movement of the sleeve to the proximal side with respect to the plunger, i.e., the movement of the injection needle to the administration position at which the injection needle projects to the distal side from the sleeve. Where the columnar portions of the respective holding portions are disposed in staggered relation, the columnar portions of one of the bolding portions are inserted into spaces defined between the columnar portions of the other holding portion. This permits the movement of the sleeve to the proximal side with respect to the plunger to reduce the total length of the sleeve and the plunger. When the sleeve and the plunger are brought into an axially contracted state, the proximal needle portion of the injection needle penetrates the gasket, and the distal needle portion of the injection needle projects to the distal side from the distal end of the sleeve.

Further, the injection needle may be a double ended needle. The injection needle may be held in an axially movable manner by the plunger and the sleeve, and may be axially spaced away from the gasket to the distal side during the storage before the administration. The plunger includes a tubular attachment portion provided at the proximal end thereof. The gasket is air-tightly fitted around the tubular attachment portion, and a plug is air-tightly fitted in the tubular attachment portion, whereby a sealed aseptic space is defined between the plug and the gasket and the proximal portion of the injection needle penetrates the plug to be located in the sealed aseptic space daring the storage. With this arrangement, the proximal portion of the injection needle, which penetrates the gasket to be exposed in the liquid drug during the administration of the liquid drug, is prevented from being exposed to the atmosphere to be contaminated.

Advantageous Effects of Invention

With the inventive syringe, the pushing operation is further performed after the administration of the liquid drug, making it possible to automatically retract the injection needle into the sleeve and lock the sleeve. This prevents an accident such that a patient inadvertently sticks her/his hand with the injection needle when improperly performing the needle retracting operation.

DESCRIPTION OF EMBODIMENTS

Preferred embodiments of the present invention will hereinafter be described based on the attached drawings.

Figure 1:
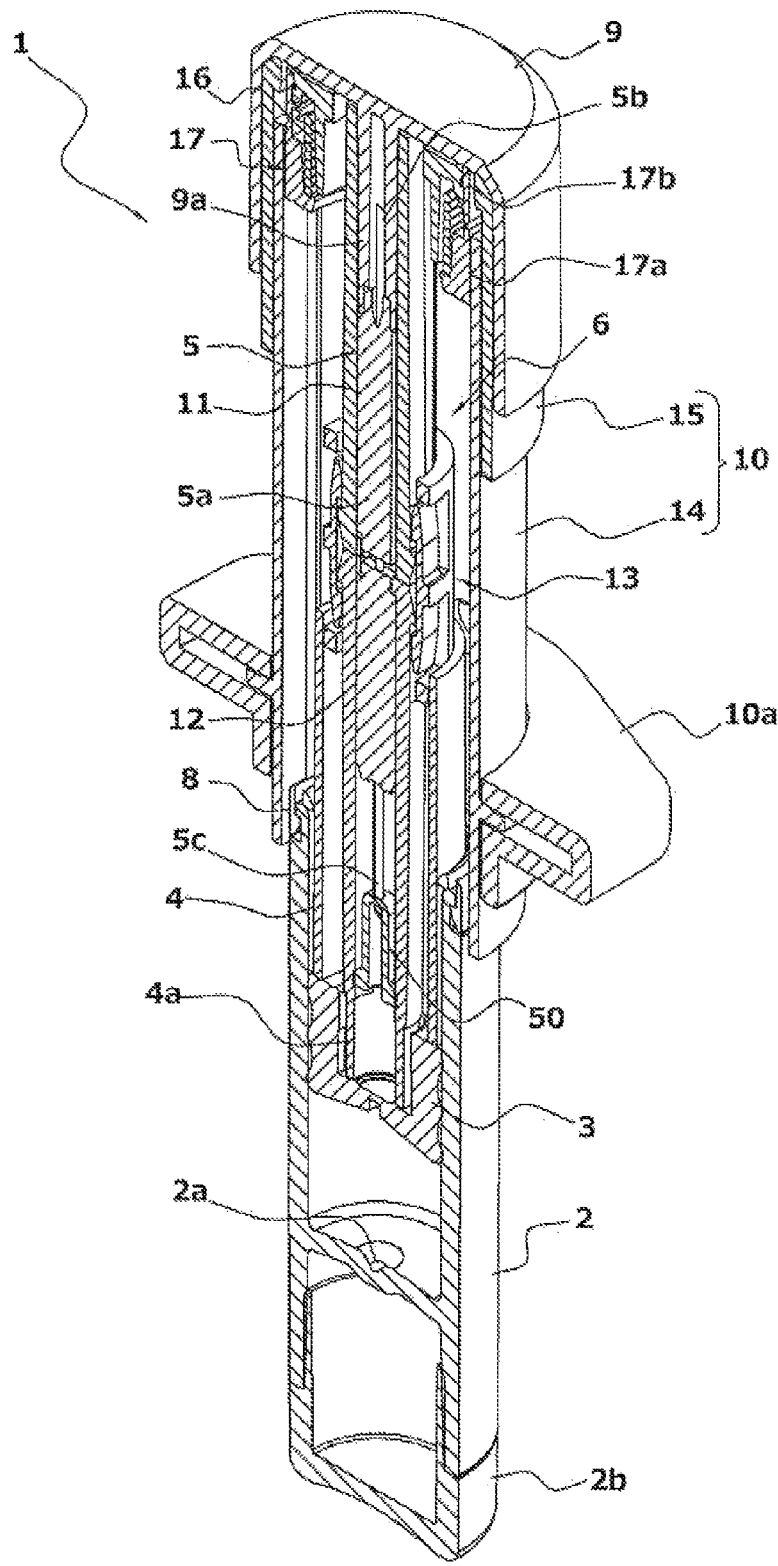
FIG. 1 is a perspective view showing a state of a syringe observed during storage partly in a vertical section (X-Z section) according to an embodiment of the present invention.
Figure 2:
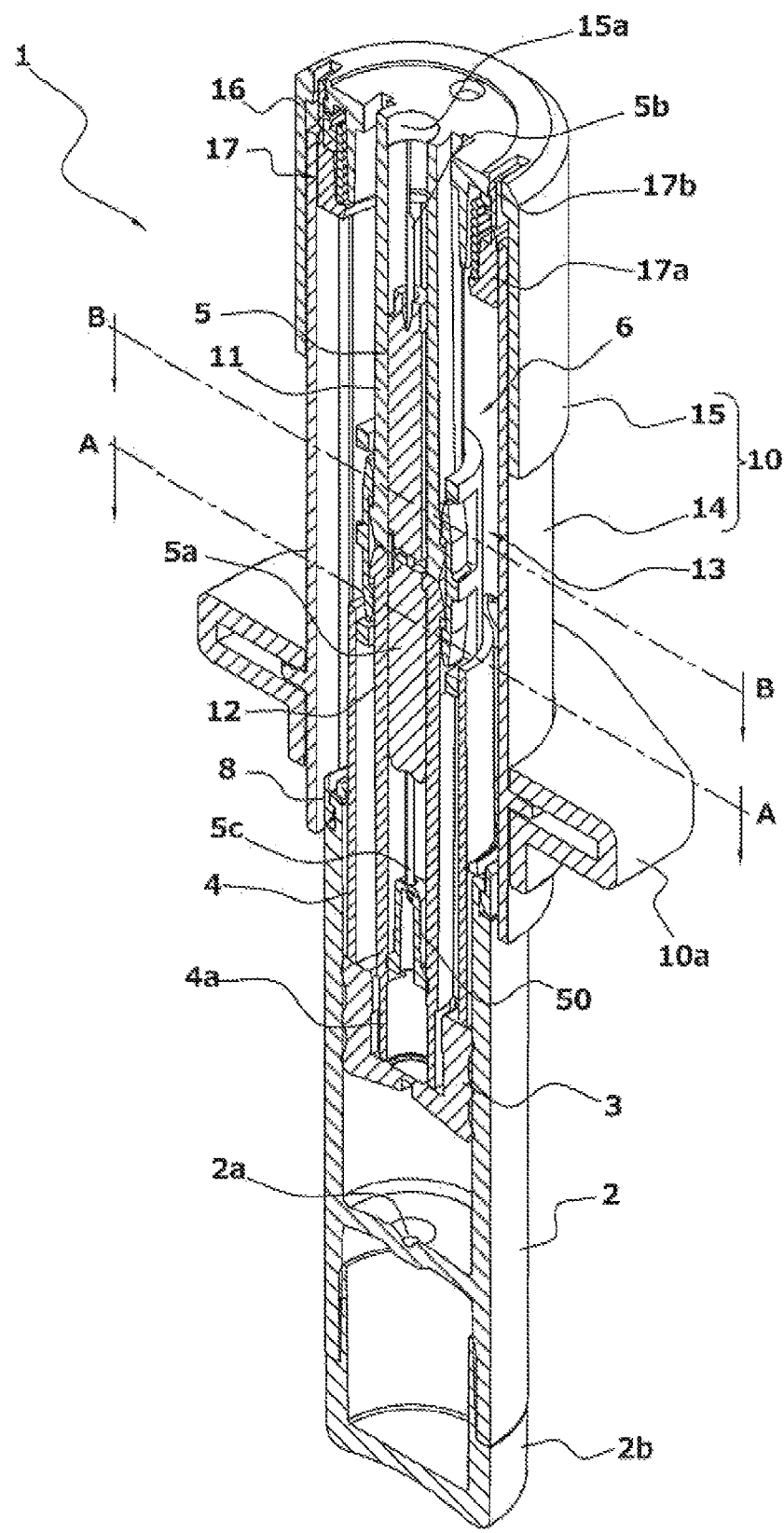
FIG. 2 is a perspective view showing the syringe partly in a vertical section (X-Z section) with its protection cap removed.
Figure 3:
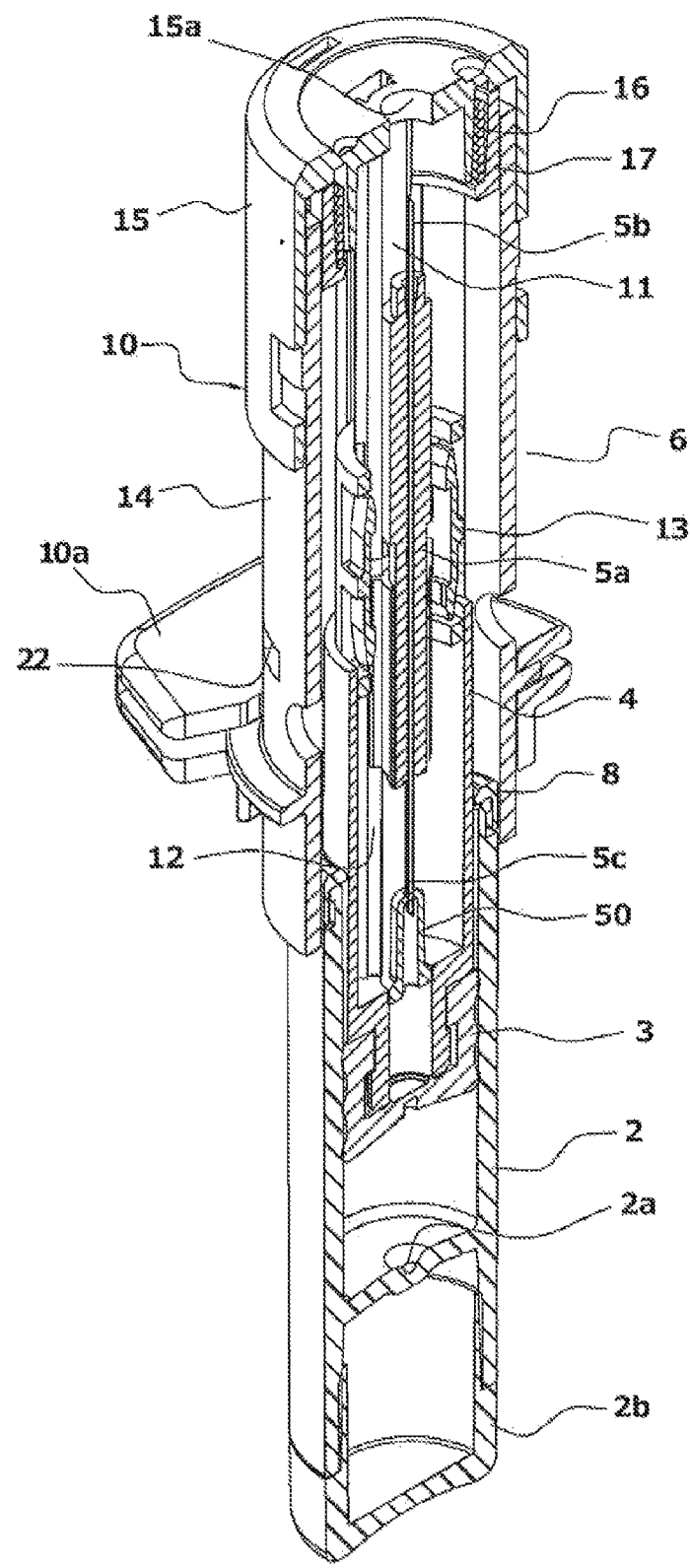
FIG. 3 is a perspective view showing the syringe in the same state as in FIG. 2 partly in another vertical section (Y-Z section).

FIG. 1 shows a state of a syringe 1 observed during storage according to one embodiment of the present invention, and FIGS. 2 and 3 illustrate the syringe with a protection cap 9 removed from a distal portion for administration of a liquid drug. In FIGS. 1 and 2, the syringe is illustrated in a vertical section taken slightly eccentrically from its axis.

In FIG. 3, the syringe is illustrated in a vertical section taken along its axis. The term "distal side" is herein defined as a distal side of an injection needle, and the term "proximal side" is herein defined as a proximal side of the injection needle. That is, the upper side is the distal side, and the lower side is the proximal side in the attached drawings.

The syringe 1 according to this embodiment includes a bottomed tubular syringe barrel 2 made of a transparent or translucent glass or synthetic resin, a gasket 3 inserted into the syringe barrel 2 from a distal end opening to close the syringe barrel 2 in an axially movable manner, a plunger 4 which pushes the gasket 3 to the proximal side, a double-ended injection needle 5 attached to the plunger 4 in an axially movable manner, and a safety operation mechanism 6 connected to the plunger 4. These components are coaxially disposed.

The syringe barrel 2 is preliminarily filled with a predetermined amount of liquid drug, and closed with the gasket 3 to seal the liquid drug therein in an aseptic room. The syringe barrel 2 has a small recess 2a provided in a canter portion of a bottom wall thereof. An end cap 2b is attached to a proximal portion of the syringe barrel 2. The end cap 2b substantially increases the axial length of the syringe barrel 2 to prevent the proximal portion of the syringe barrel 2 from being nested in a sleeve 10 when the syringe barrel 2 is fully pushed in. A ring-shaped stopper 8 is attached to the distal end opening of the syringe barrel 2 for preventing the gasket 3 from coming off from the syringe barrel 2. The stopper 8 has an inner diameter that is smaller than the inner diameter of the syringe barrel 2 and greater than the outer diameter of the plunger 4.

The gasket 3 is air-tightly fitted around a tubular attachment portion 4a of the plunger 4. A center axis portion of the gasket 8 has a smaller thickness so as to be easily pierced with a proximal needle portion 5c of the injection needle 5. A gasket disclosed by the inventor of the present invention in JP-2012-228335-A may be used as the gasket 3. Further, a rubber plug 50 is air-tightly fitted in the tubular attachment portion 4a. Thus, a sealed aseptic space is defined between the plug 50 and the gasket 3. During the storage before the administration of the liquid drug, the injection needle 5 is axially spaced away from the gasket 3 to the distal side, and a proximal end of the proximal needle portion 5c of the injection needle 5 pierces the plug 50 to be located in the sealed aseptic space.

The plunger 4 has a hollow space axially extending therein, and the injection needle 5 is fitted in the plunger 4 in an axially movable manner.

The injection needle 5 includes a columnar needle base 5a, and a needle tube axially extending through the needle base 5a. The needle tube projects from axially opposite ends of the needle base 5a. A portion of the needle tube projecting to the distal side serves as a distal needle portion 5b, and a portion of the needle tube projecting to the proximal side serves as the proximal needle portion 5c. The needle portions 5b, 5c each have a sharp edge provided at an end thereof.

The safety operation mechanism 6 prevents inadvertent or careless operation to prevent an accident from being caused by the injection needle 5. In this embodiment, the safety operation mechanism 6 includes a cap-shaped sleeve 10 fitted around the syringe barrel 2 from the distal side in an axially movable and rotatable manner, a first holding portion 11 provided integrally with the sleeve 10 and fitted around the needle base 5a from the distal side, a second holding portion 12 provided integrally with the plunger 4 and fitted around the needle base 5a from the proximal side, and a key cylinder 13 fitted around the first and second holding portions 11, 12. Further, a protection cap 9 is removably attached to a distal portion of the sleeve 10.

The sleeve 10 includes a cylindrical main body 14 having an axially middle portion around which a finger hook flange 10a is fitted, and a safety cover 15 attached to a distal portion of the main body 14. The safety cover 15 is engaged with the main body 14 so as to be nonrotatable with respect to the main body 14 and axially slightly movable with respect to the main body 14. During the storage and during the administration of the liquid drug, the safety cover 15 is engaged with the main body 14 to be located at a compression position (see FIG. 16) such that the safety cover 15 and the main body 14 are kept in an axially contracted state. After the administration, the safety cover 15 is moved to an extension position (see FIG. 17) such that the safety cover 15 and the main body 14 are kept in an axially extended state.

The safety cover 15 has a needle accommodating hole 15a formed in a center axis portion of a top plate thereof as shown in FIGS. 2 and 3. The injection needle 5 is moved in and out through the needle accommodating hole 15a. As shown in FIG. 1, the protection can 9 integrally includes a cylindrical plug portion 9a fitted in the needle accommodating hole 15a and air-tightly fitted around the distal needle portion 5b of the injection needle 5 accommodated in the sleeve 10, whereby the distal needle portion 5b of the injection needle 5 is isolated from outside air for prevention of contamination of the needle 5b during the storage.

Figure 4:
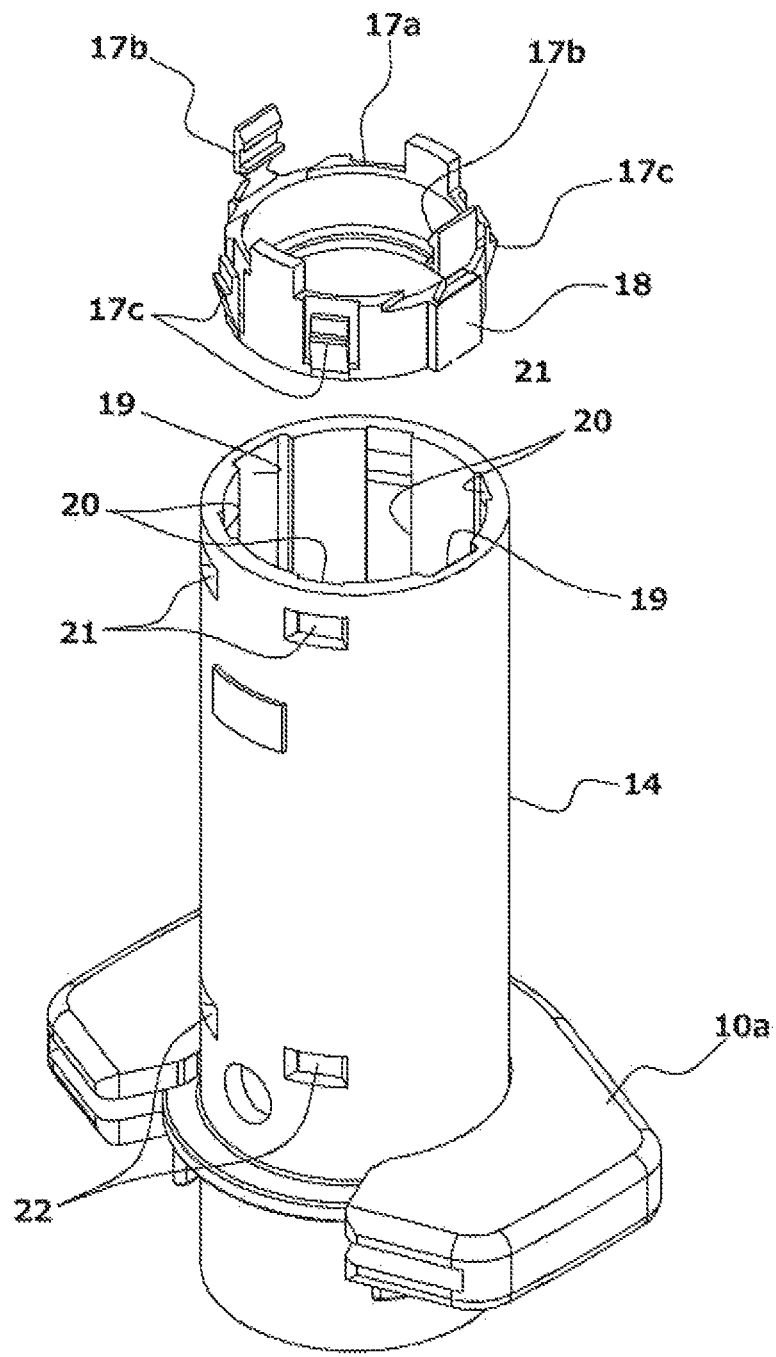
FIG. 4 is an exploded perspective view of a sleeve main body and a spring holder of the syringe.

A coil spring 16 and a spring holder 17 which holds the spring 16 in an axially compressed state are provided in the safety cover 15. The spring holder 17 includes a ring portion 17a axially opposed to an upper open face of the distal end opening of the syringe barrel 2, and lock pieces 17b (lock portions) axially locked to the top plate of the safety cover 15. More specifically, as shown in FIG. 4, the lock pieces 17b are provided in pair in diametrically opposed relation. The lock pieces 17b are provided integrally with the ring portion 17a to be connected to the ring portion 17a via thin narrow connection portions which are easily breakable. The coil spring 16 is held in the compressed state between the top plate of the safety cover 15 and the ring portion 17a. The connection portions are each designed to have a strength such that the connection portions are broken neither by the biasing force of the coil spring 16 nor by a pushing force to be applied thereto for the administration of the liquid drug. The ring portion 17a has projections 18 provided at predetermined circumferential positions on an outer periphery thereof. The main body 14 has guide channels 19 provided in an inner peripheral surface thereof as axially extending for receiving the projections 18 in an axially slidable manner, whereby the ring portion 17a is held in the main body 14 in an axially movable and nonrotatable manner.

As shown in FIG. 4, the main body 14 further has a plurality of engagement channels 20 (four engagement channels 20 in FIG. 4) provided at predetermined circumferential positions in the inner surface thereof as extending axially. A first engagement recess 21 and a second engagement recess 22 are provided in axially spaced relation in each of the engagement channels 20. In this embodiment, the engagement recesses 21, 22 are each formed as a through-hole. The ring portion 17a has resilient engagement pieces 17c provided on the enter periphery thereof to be axially engaged with the first engagement holes 21 so as to lock the safety cover 15 at the compression position. The engagement pieces 17c are circumferentially disposed in association with the engagement channels 20. The engagement pieces 17c each have a proximal portion connected to a proximal portion of the ring portion 17a, and a distal portion radially expansible. The engagement pieces 17o further each have a distal engagement step, and an outer inclined surface having a radius progressively reduced toward a proximal edge thereof. With the engagement steps of the engagement pieces 17c in engagement with distal edges of the engagement holes 21 or 22, the main body 14 is prevented from being moved to the proximal side with respect to the ring portion 17a. When the ring portion 17a is moved to the proximal side with respect to the main body 14, the engagement pieces 17c are guided by their inclined surfaces to be resiliently deformed radially inward, and guided through the engagement channels 20 to be slid to the proximal side with respect to the main body 14. With the engagement pieces 17c in engagement with the second engagement holes 22, however, the syringe barrel 2, the gasket 3, the plunger 4 and the safety cover 15 prevent the ring portion 17a from being further moved to the proximal side with respect to the main body 14.

Figure 5:
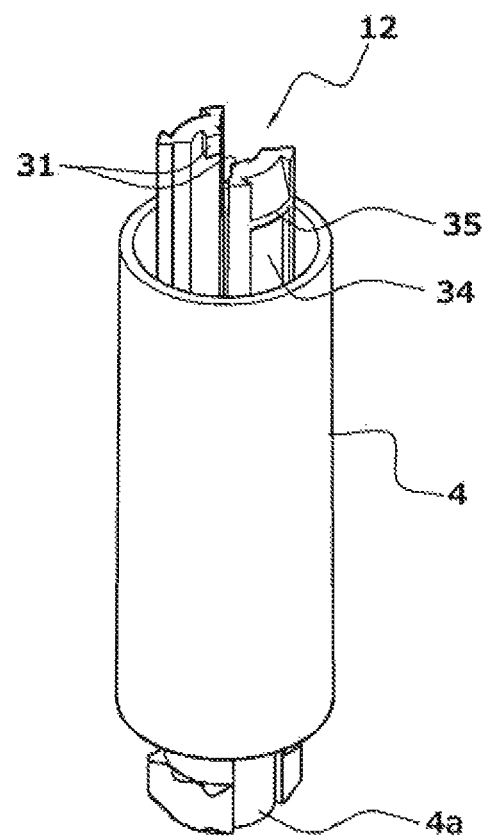
FIG. 5 is a perspective view of a plunger of the syringe.
Figure 6:
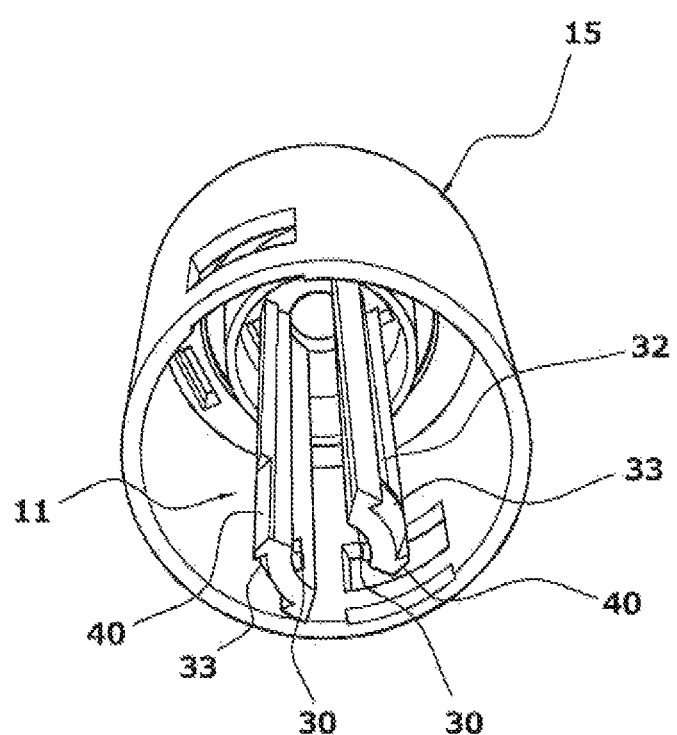
FIG. 6 is a perspective view of a safety cover of the syringe as seen from a proximal side.
Figure 12:
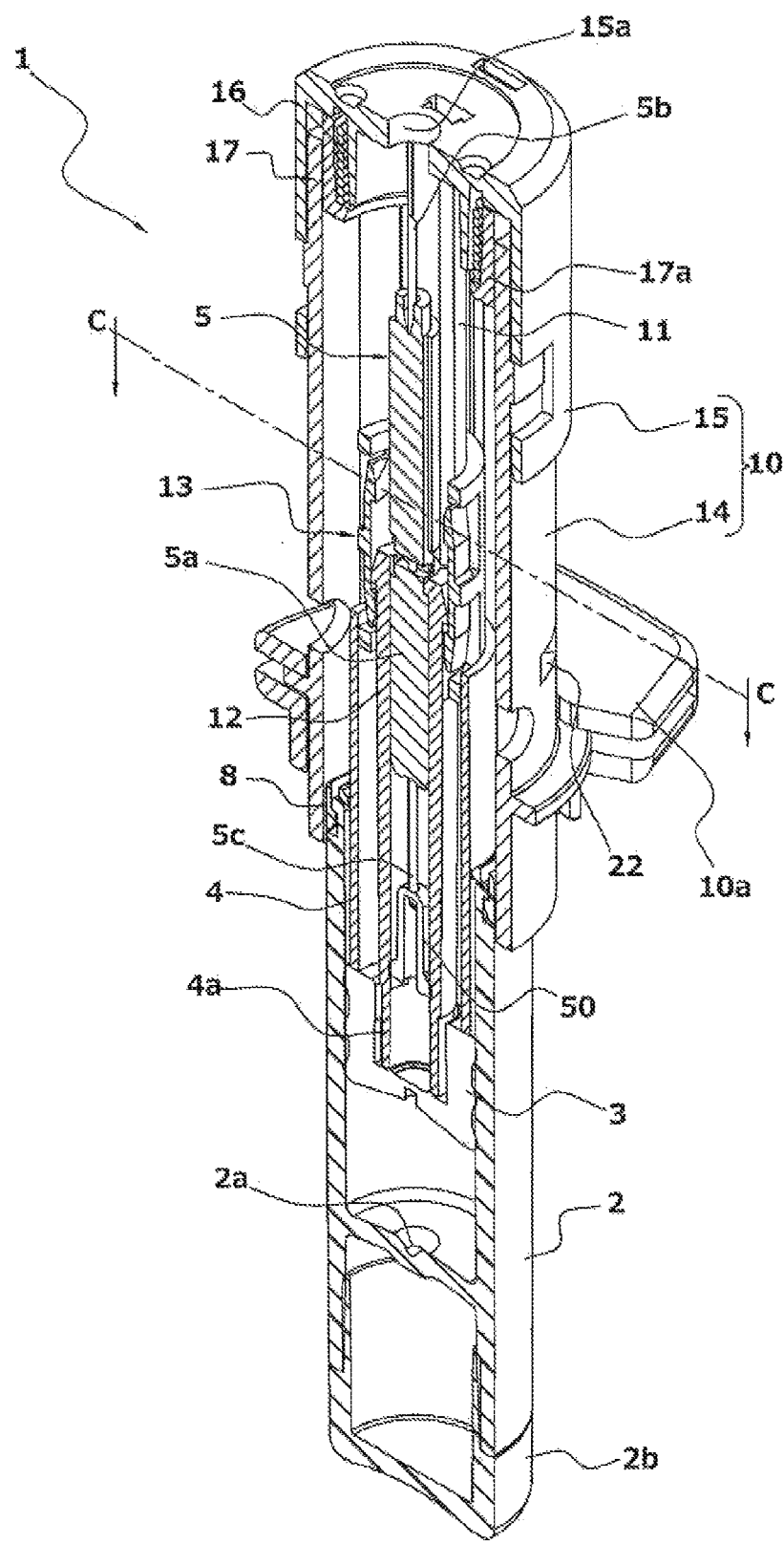
FIG. 12 is a perspective view showing a state of the syringe rotated 90 degrees from the state of FIG. 2 partly in a vertical section.
Figure 14:
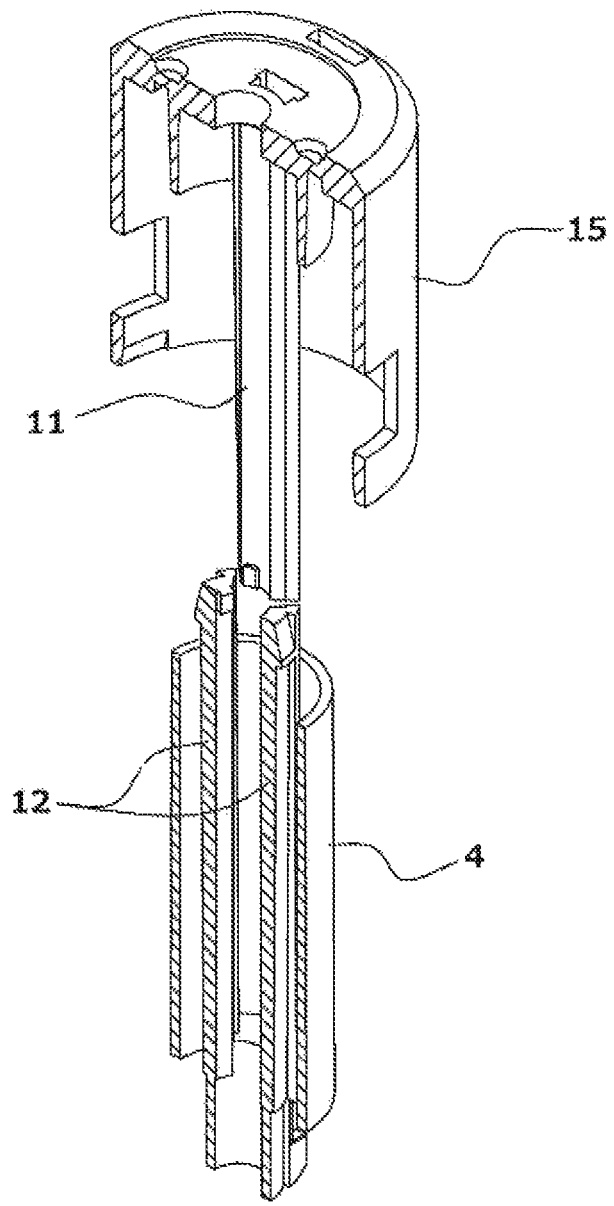
FIG. 14 is a perspective view showing a relationship between the plunger and the sleeve of the syringe in the state shown in FIG. 12.

As shown in FIGS. 5 and 6, the first and second holding portions 11, 12 each include a pair of axially elongated columnar portions provided in diametrically opposed relation and each having an arcuate cross sectional shape. The holding portions 11, 12 hold the needle base 5a therein with the columnar portions thereof in contact with an outer peripheral surface of the needle base 5a. During the storage, as shown in FIGS. 2 and 3, proximal end faces of the columnar portions of the first holding portion 11 respectively abut against distal end faces of the columnar portions of the second holding portion 12, so that the total length of the first and second holding portions is greater than the overall length of the injection needle 5. In this extended state, the first and second holding portions are axially locked with respect to each other to prevent the sleeve 10 from being moved to the proximal side with respect to the plunger 4. With the sleeve 10 rotated about 90 degrees with respect to the plunger 4, on the other hand, the columnar portions of the holding portions are located in staggered relation as shown in FIGS. 12 and 14, so that the columnar portions of one of the holding portions can be inserted into spaces defined between the columnar portions of the other holding portion. This permits the movement of the sleeve 10 to the proximal side with respect to the plunger 4 to reduce the total length of the sleeve 10 and the plunger 4. With the sleeve 10 and the plunger 4 thus kept in an axially contracted, state, the proximal needle portion 5c of the injection needle 6 penetrates the gasket and, at the same time, the distal needle portion 5b projects from the needle accommodating hole 15a of the sleeve 10 to the distal side.

Figure 7:
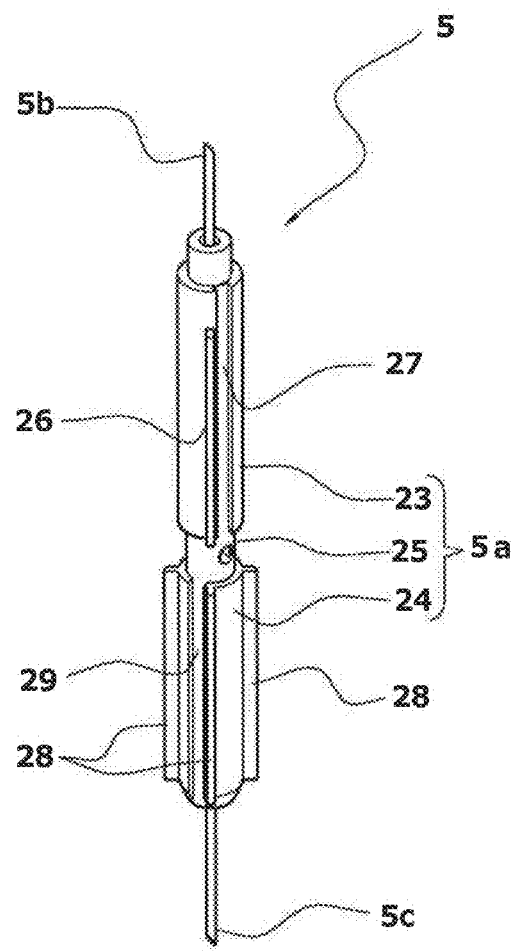
FIG. 7 is a perspective view of an injection needle of the syringe.

Further, as shown in FIG. 7, the needle base 5a of the injection needle 5 includes a first axial portion 23 around which the first holding portion 11 is fitted at the distal side during the storage, a second axial portion 24 around which the second holding portion 12 is fitted at the proximal side, and a smaller diameter axial portion 25 provided between the first axial portion 23 and the second axial portion 24.

The first axial portion 23 has a pair of restriction ribs 26 provided in diametrically opposed relation on an outer peripheral surface thereof to be brought into abutment against circumferential edges of the respective columnar portions of the first holding portion 11 so as to permit relative rotation of the first holding portion 11 within an about 90-degree range with respect to the first axial portion 23 but prevent relative rotation of the first holding portion 11 by greater than about 90 degrees. The first axial portion 23 further includes a pair of channels 27 provided in diametrically opposed relation in the outer peripheral surface thereof as extending along the entire axial length thereof. The second axial portion 24 includes four restriction ribs 28 provided at four positions on an outer peripheral surface thereof to be brought into abutment against circumferential edges of the respective columnar portions of the second holding portion 12 so as to prevent relative rotation of the second holding portion 12 with respect to the second axial portion 24. The second axial portion 24 further includes a pair of channels provided in the outer peripheral surface thereof as extending along the entire axial length thereof. As shown in FIG. 6, the columnar portions of the first holding portion 11 each have a key 30 provided in the form of a projection on a proximal inner surface portion thereof. As shown in FIG. 5, the columnar portions of the second holding portion 12 each have a key 31 provided in the form of a projection on a distal inner surface portion thereof.

In an initial state during the storage, the keys 30, 31 are located around the smaller diameter axial portion 25. The keys 30 of the first holding portion 11 are axially engaged with a step defined between the smaller diameter axial portion 25 and the first axial portion 23, and the keys 31 of the second holding portion 12 are axially engaged with a step defined between the smaller diameter axial portion 25 and the second axial portion 24. Thus, the axial movement of the injection needle 5 with respect to the first and second holding portions 11, 12 is prevented. During the storage, the keys 31 of the second holding portion 12 are located in axially opposed relation to the channels 27 of the first axial portion 23, and the movement of the injection needle 5 to the distal side with respect to the second holding portion 12 is permitted by rotating the first holding portion 11 by about 90 degrees. At this time, the keys 31 are axially moved in the channels 27. On the other hand, the keys 30 of the first holding portion 11 are offset about 90 degrees from the channels 29 of the second axial portion 24 during the storage. When the first holding portion 11 is rotated about 90 degrees with respect to the injection needle 5, the keys are brought into axially opposed relation to the channels 29, thereby permitting relative movement of the first holding portion 11 to the distal side with respect to the injection needle 5. At this time, the keys 30 are axially moved in the channels 29.

Figure 15:
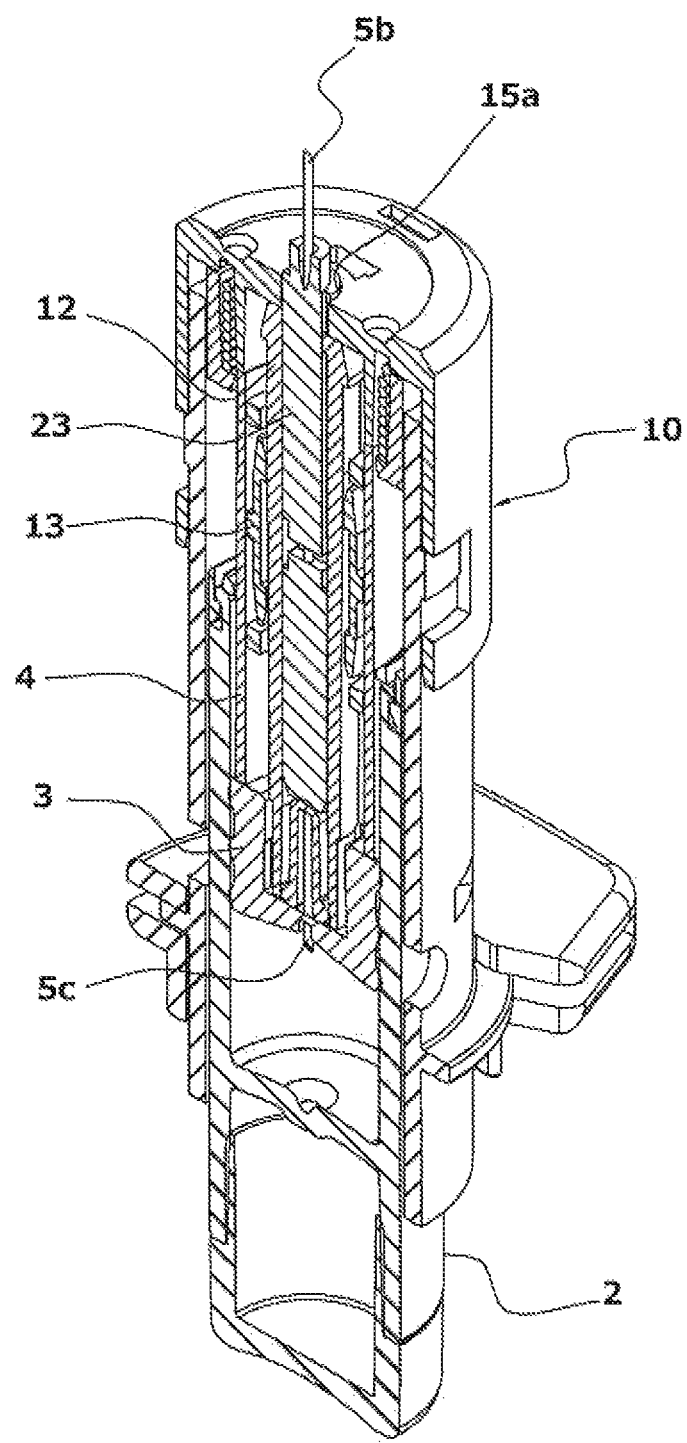
FIG. 15 is a perspective view showing the syringe partly in a vertical section with the injection needle projecting for administration of a liquid drug.

When the sleeve 10 is rotated 90 degrees with respect to the syringe barrel 2 from the initial state and pushed, the first holding portion 11 is axially pushed with respect to the injection needle 5. As a result, the distal needle portion 5b of the injection needle 5 projects from the needle accommodating hole 15a of the sleeve 10 as shown in FIG. 15. At this time, distal portions of the restriction ribs 26 of the first axial portion 23 axially abut against the top plate of the sleeve 10 around the needle accommodating hole 15a. Thus, the injection needle 5 can be forcibly pushed to the proximal side toward the gasket 3.

Further, as shown in FIG. 6, the first holding portion 11 has engagement channels 32 provided in an outer peripheral surface thereof as extending axially, and engagement projections 33 respectively provided on proximal portions of the engagement channels 32. The engagement projections 33 each have a generally horizontal step provided along a distal edge (upper edge in FIG. 6) thereof. The engagement projections 33 each have an outer taper surface having a radius progressively reduced toward a proximal edge thereof. As shown in FIG. 5, the second holding portion 12 also has engagement channels 34 provided in an outer peripheral surface thereof as extending axially, and engagement projections 35 respectively provided on distal portions of the engagement channels 34. The engagement projections 35 each have a generally horizontal step provided along a proximal edge thereof. The engagement projections 35 each have an outer taper surface having a radius progressively reduced toward a distal edge thereof. These engagement channels 32, 34 are respectively engaged with look pieces 36, 37 of the key cylinder 13.

Figure 8:
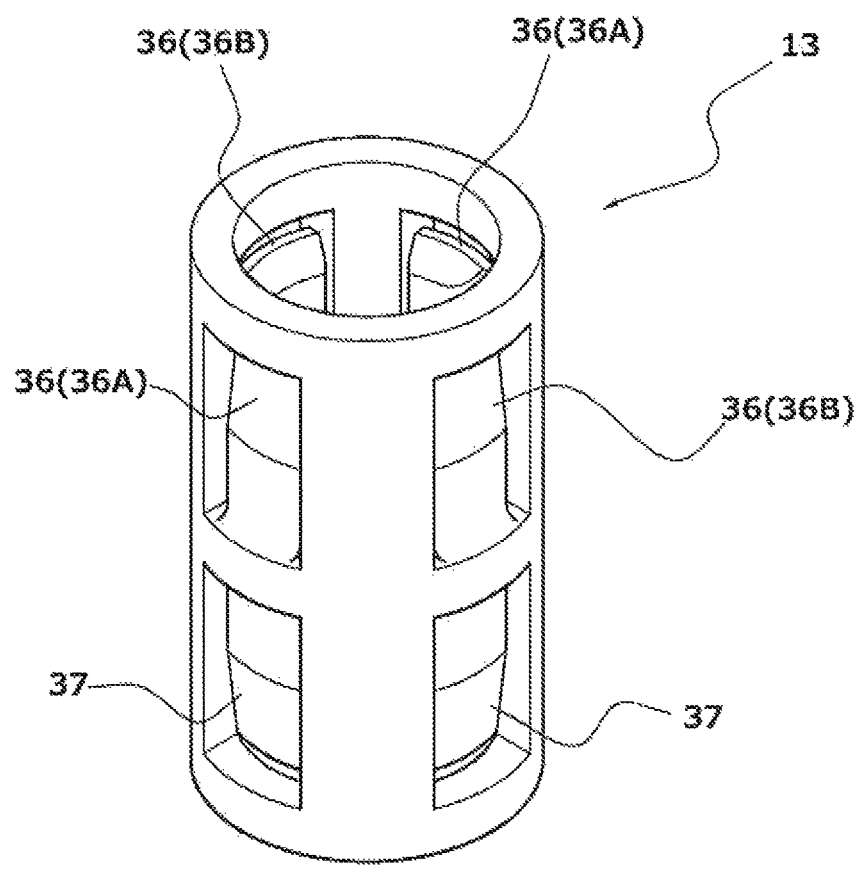
FIG. 8 is a perspective view of a key cylinder of the syringe.
Figure 9:
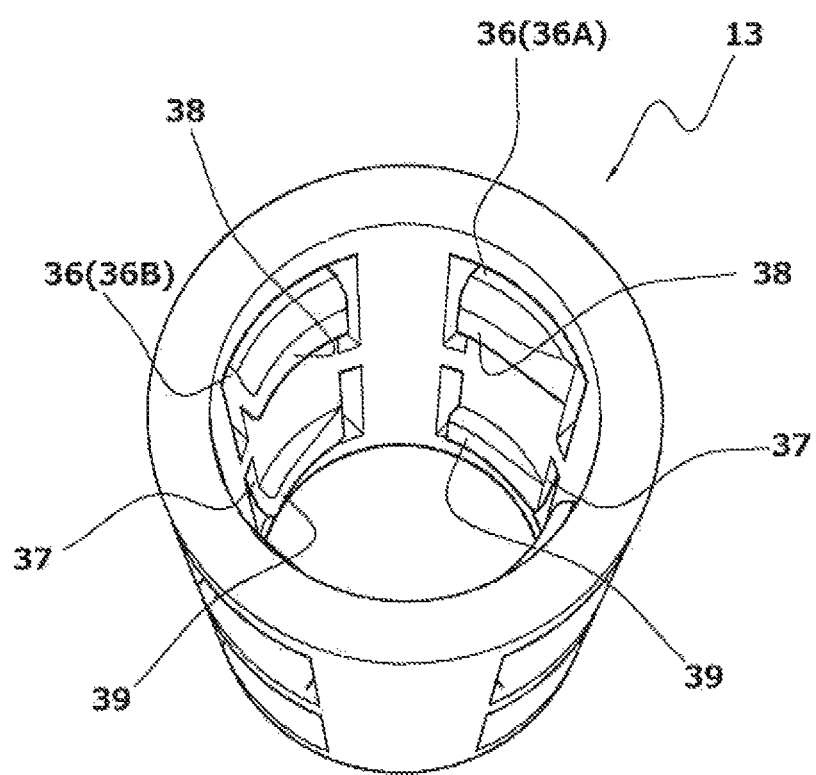
FIG. 9 is a perspective view of the key cylinder of the syringe as seen from a distal side.

As shown in FIGS. 8 and 9, the key cylinder 13 has a generally cylindrical shape, and includes four lock pieces 36 circumferentially arranged in a distal half region thereof and four look pieces 37 circumferentially arranged in a proximal half region thereof. The distal lock pieces 36 extend to the distal side from an axially middle portion of the key cylinder 13, and distal portions of the lock pieces 36 are resiliently deformable to be radially expanded. The proximal lock pieces 37 extend to the proximal side from the axially middle portion of the key cylinder 13, and proximal portions of the look pieces 37 are resiliently deformable to be radially expanded.

The distal lock pieces 36 respectively have engagement projections 38 provided on inner surfaces thereof to be engaged with the engagement channels 32 of the first holding portion 11 so as to permit the axial movement and prevent the relative rotation. The engagement projections 38 respectively have steps provided along proximal edges thereof to be engaged with the engagement projections 33 of the first holding portion 11. Further, distal portions of the engagement projections 38 each have an inner taper surface having a radius progressively increased toward a distal edge thereof. The proximal lock pieces 37 respectively have engagement projections 39 provided on inner surfaces thereof to be engaged with the engagement channels 34 of the second holding portion 12 to permit the axial movement and prevent the relative rotation. The engagement projections 39 respectively have steps provided along distal edges thereof to be engaged with the engagement projections 35 of the second holding portion 12 from the proximal side. Further, proximal portions of the engagement projections 39 each have an inner taper surface having a radius progressively increased to a proximal edge thereof.

With the provision of the taper surfaces, the proximal portions of the first holding portion 11 can be axially moved over the proximal lock pieces 37 of the key cylinder 13, and the distal portions of the second holding portion 12 can be axially moved over the distal lock pieces 36 of the key cylinder 13. With the provision of the steps, on the other hand, the proximal portions of the first holding portion 11 are axially engaged with the distal lock pieces 36, and the distal portions of the second holding portion 12 are axially engaged with the proximal lock pieces 37.

As shown, the first holding portion 11 is configured to be rotatable 90 degrees counterclockwise from the initial position with respect to the key cylinder 13 and locked at the 90-degree rotated position with respect to the rotation direction. Out of the distal four lock pieces 36 of the key cylinder 13, two lock pieces 36A to be engaged with the engagement channels 32 of the first holding portion 11 each have an inner peripheral surface which is circumferentially inclined to have a radius progressively increased clockwise as also shown in FIG. 9. With this arrangement, the lock pieces 36A are circumferentially detachable from the engagement channels 32 by rotating the first holding portion 11 counterclockwise with respect to the key cylinder 13. As shown in FIG. 6, the first holding portion 11 has inclined surfaces 40 provided on outer surface edge portions thereof defined with aspect to the rotation direction (counterclockwise direction). When the first holding portion 11 is rotated, the other two lock pieces 36B are pushed up by the inclined surface 40, making it possible to insert the lock pieces 36B into the engagement channels 32. These two lock pieces 36B each have no circumferentially inclined inner surface, so that the lock pieces 36B are circumferentially disengageable from the engagement channels 32 after having been respectively engaged with the engagement channels 32.

On the other hand, the key cylinder 13 is connected to the second holding portion 12 so as to be rotatable in one direction (clockwise). That is, as shown in FIG. 9, the inner surfaces of the four proximal lock pieces 37 of the key cylinder 13 are inclined as having a radius progressively increased clockwise. Therefore, the lock pieces 37 are circumferentially disengageable from the engagement channels 34 by rotating the key cylinder 13 clockwise with respect to the second holding portion 12. At the same time, the next lock pieces 37 can be inserted into the engagement channels 34.

Next, the operation of the syringe 1 according to this embodiment will be described.

During the storage, the distal portion 5b of the injection needle 5 is isolated from the atmosphere by the plug portion 9a of the protection cap 9, and the proximal portion 5c of the injection needle 5 is isolated from the atmosphere by the gasket 3 and the plug 50. The liquid drug in the syringe barrel 2 is isolated from the atmosphere by the gasket 3. Therefore, the liquid drug and the opposite end portions of the injection needle are protected from contamination by delivering the syringe in a sterilized state.

Figure 10:
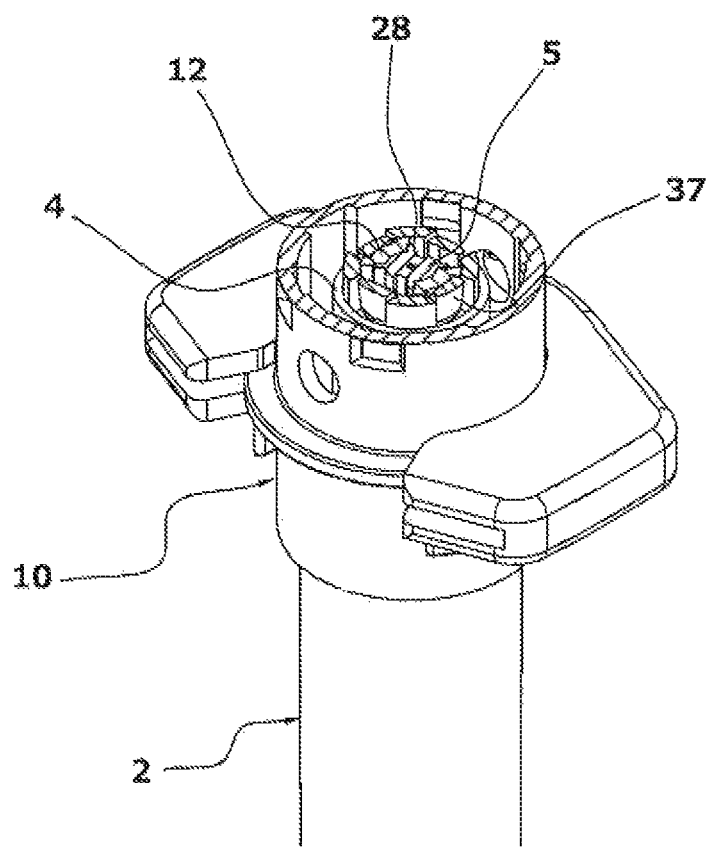
FIG. 10 is a perspective view partly in section taken along an A-A line in FIG. 2.
Figure 11:
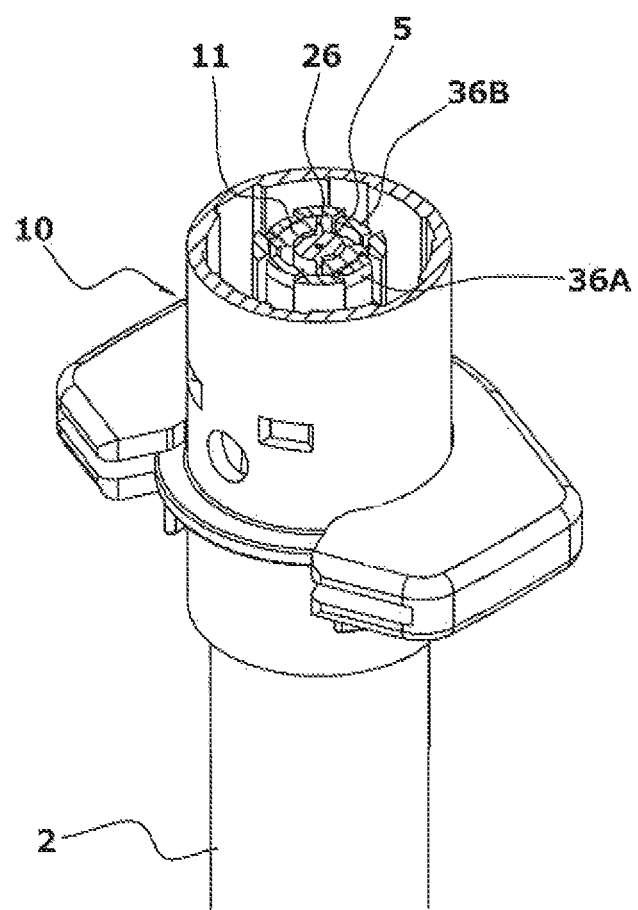
FIG. 11 is a perspective view partly in section taken along a B-B line in FIG. 2.

When the liquid drug is to be administered by a user, the protection cap 9 is first removed, and then the sleeve 10 is rotated 90 degrees counterclockwise with respect to the syringe barrel 2 from the initial state shown in FIGS. 2 and 3 to a state shown in FIG. 12. At this time, the rotation of the plunger 4 is restricted by a frictional force of the gasket 3 with respect to the syringe barrel 2. As shown in FIG. 10, the rotation of the injection needle 5 fitted in the second holding portion 12 of the plunger 4 with respect to the second holding portion 12 is restricted by the restriction ribs 28. The lock pieces 37 of the key cylinder 13 are engaged counterclockwise with the engagement channels 34 of the second holding portion 12 to be locked, whereby the rotation of the key cylinder 13 is also restricted. On the other hand, as shown in FIG. 11, the first holding portion 11 is rotatable 90 degrees counterclockwise with respect to the injection needle 5, and rotatable 90 degrees counterclockwise with respect to the key cylinder 13. Therefore, the first holding portion 11 is rotated 90 degrees with respect to the second holding portion 12, the injection needle 5 and the key cylinder 13.

Figure 13:
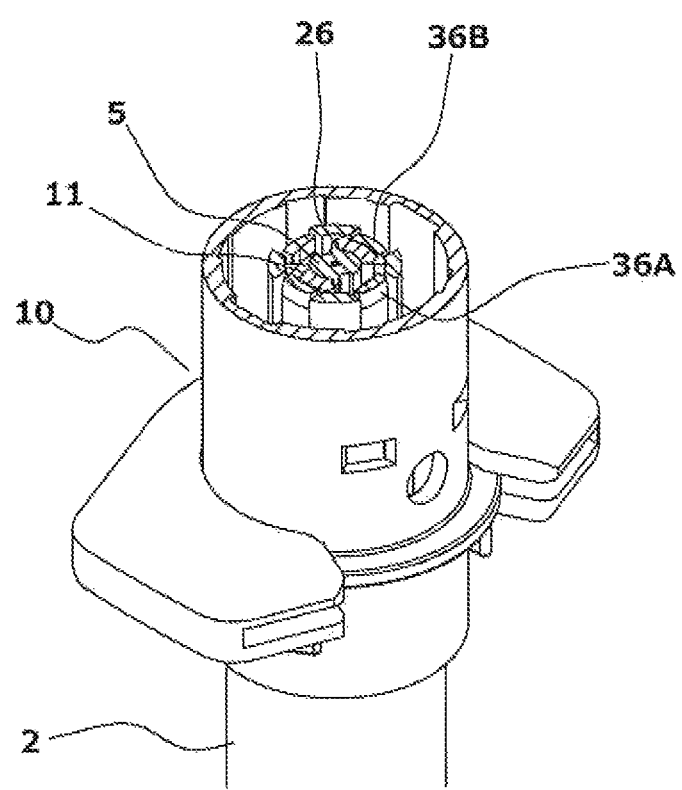
FIG. 13 is a perspective view partly in section taken along a C-C line in FIG. 12.

By this operation, the sleeve 10 is rotated to the state shown in FIG. 12, whereby the first holding portion 11 and the key cylinder 13 are locked in the rotation direction as shown in FIG. 13. In this state, as shown in FIG. 14, the first holding portion 11 and the second holding portion 12 can be engaged with each other. Further, the first holding portion 11 can be pushed to the proximal side with respect to the injection needle 5, and the injection needle 5 can be pushed to the proximal side with respect to the second holding portion 12.

Next, the proximal portion of the syringe barrel 2 is pushed to the distal side with respect to the sleeve 10 to the state shown in FIG. 15. At this time, the proximal portions of the first holding portion 11 are axially moved over the lock pieces 37 of the key cylinder 13, and the distal portions of the second holding portion 12 are axially moved over the lock pieces 36 of the key cylinder 13, whereby the key cylinder 13 is fitted around an axially middle portion of a combination of the first and second holding portions 11, 12 engaged with each other in axially overlapping relation. Further, the injection needle 5 is forcibly pushed to the proximal side with respect to the syringe barrel 2 by pushing the syringe barrel 2. Thus, the proximal needle portion 5c penetrates the gasket 3, whereby the inside of the syringe barrel 2 communicates with the liquid drug containing space to permit the administration of the liquid drug through the injection needle 5. At this time, the distal portions of the plunger 4 are axially engaged with the top plate of the safety cover 15, permitting stable pushing operation of the plunger 4 with respect to the syringe barrel 2.

Figure 16:
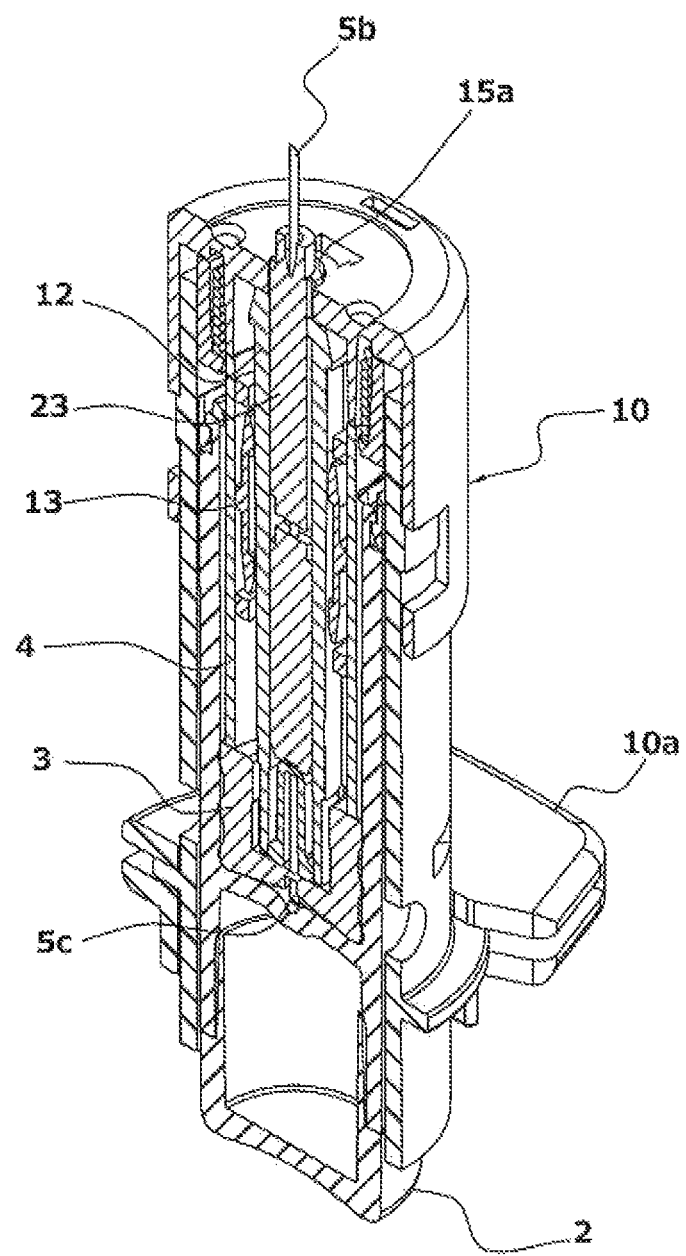
FIG. 16 is a perspective view showing a state of the syringe observed immediately after the administration of the liquid drug partly in a vertical section.

Then, an injection site of a human body is stuck with the distal needle portion 5b of the injection needle 5 projecting to the distal side, and the syringe barrel 2 is pushed with respect to the sleeve 10, whereby the volume of the inside space of the syringe barrel 2 is reduced to administer the liquid drug to the human body. The syringe barrel 2 is further pushed to an administration completion position as shown in FIG. 16.

Figure 17:
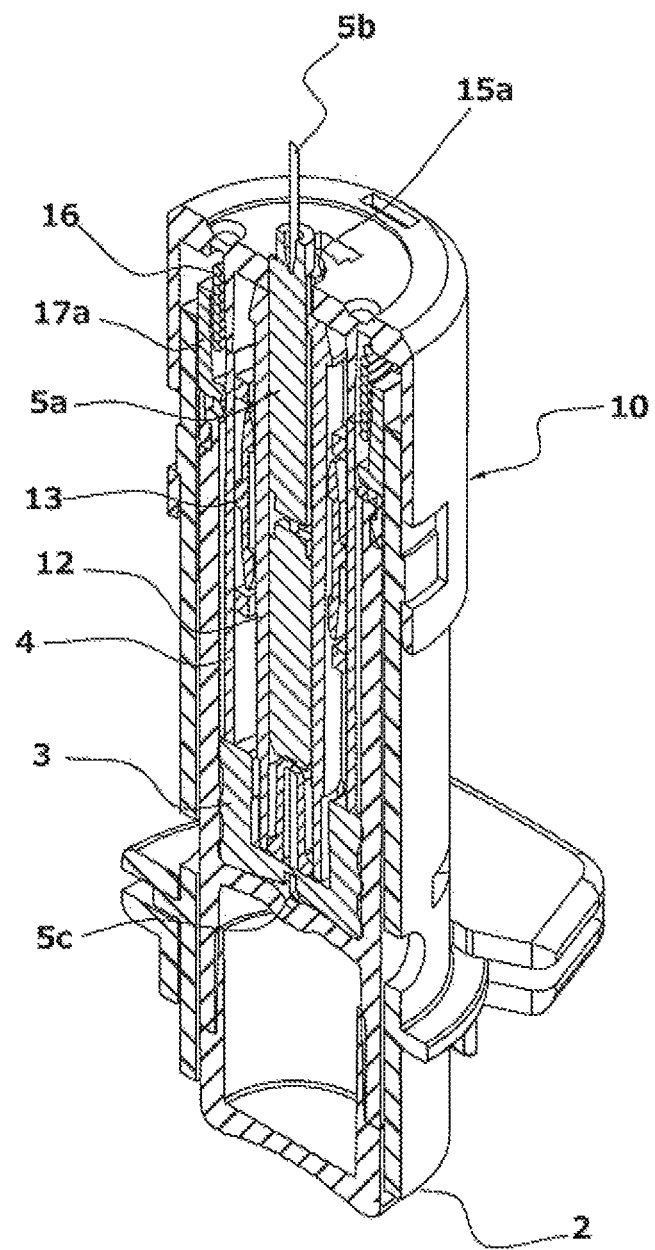
FIG. 17 is a perspective view showing the syringe partly in a vertical section with the syringe barrel strongly pushed to release a coil spring.

After the completion of the administration, the injection needle 5 is removed from the injection site with user's fingers hooked on the flange 10a and the proximal portion of the syringe barrel 2 and, in this state, the syringe barrel 2 is further strongly pushed to the distal side with respect to the sleeve main body 14. Thus, the pushing force acts on the spring holder 17 via the gasket 2, the plunger 4 and the safety cover 15, whereby the safety cover 15 is forcibly pushed to the distal side with respect to the main body 14 to break the connection portions of the lock pieces 17b. Thus, the coil spring 16 is released as shown in FIG. 17.

Figure 18:
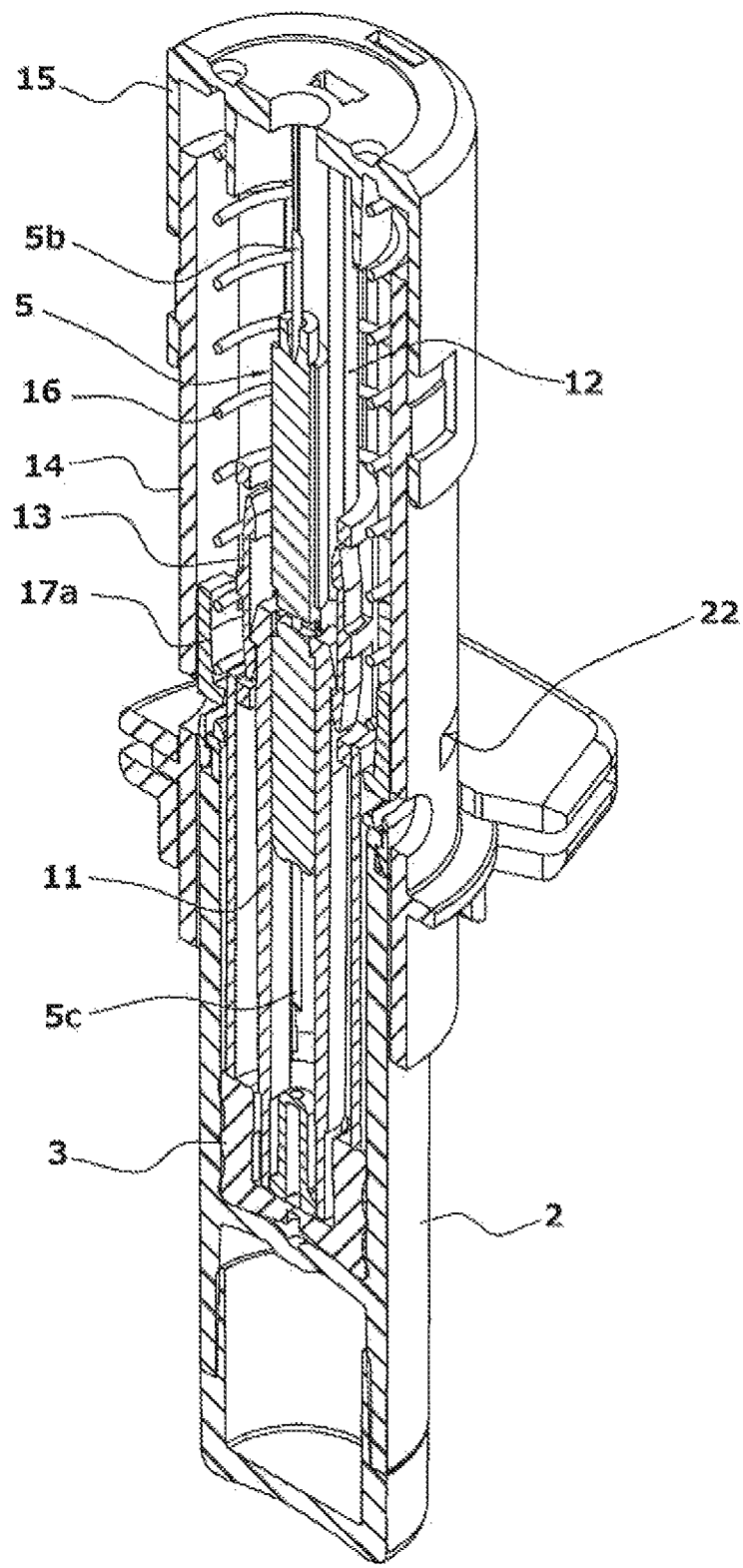
FIG. 18 is a perspective view showing the syringe partly in a vertical section with the injection needle accommodated therein by a biasing force of the coil spring.

When the pushing of the syringe barrel 2 is thereafter stopped, the ring portion 17a is moved to the proximal side with respect to the main body 14 by the biasing force of the coil spring 16. At the same time, the syringe barrel 2 is pushed to the proximal side with respect to the sleeve 10 by the ring portion 17a and, as, shown in FIGS. 18 and 19, the first holding portion 11 of the sleeve 10 and the second holding portion 12 of the plunger 4 are brought into the extended state again. Thus, the injection needle 5 is returned by the first holding portion 11 to be detached from the gasket 3, whereby the injection needle 5 is accommodated within the first and second holding portions 11, 12. In this state, the first and second holding portions 11, 12 are prevented from being axially moved away from each other by the engagement with the key cylinder 13. Further, the space defined between the gasket 2 3} and the syringe barrel 3 2} is substantially air-tightly sealed by removing the injection needle 5 from the gasket 2 3}, whereby a negative pressure prevents the syringe barrel 2 from being extracted to the proximal side with respect to the gasket 3. Thus, the syringe barrel 2 and the sleeve 10 are axially engaged indirectly with each other, so that the sleeve 10 is prevented from being moved to the distal side with respect to the syringe barrel 2 to come off.

Figure 19:
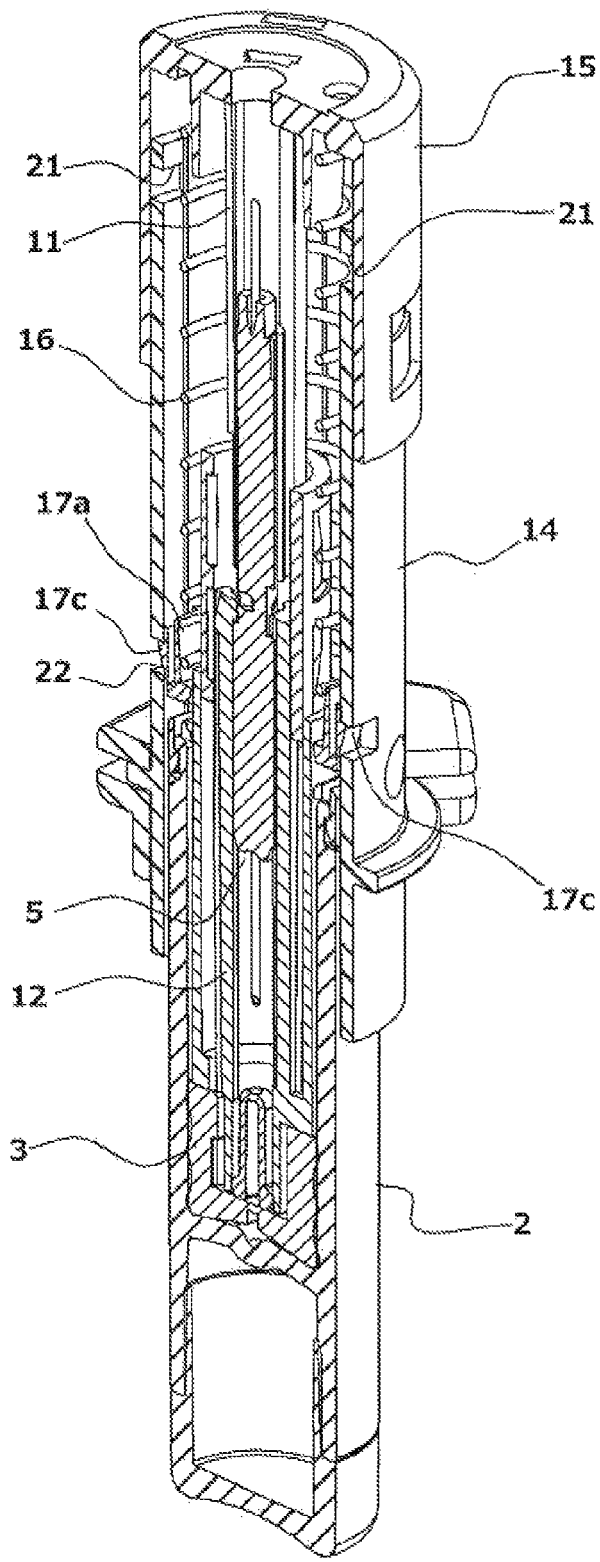
FIG. 19 is a perspective view of the syringe in the same state as in FIG. 18 partly in a vertical section (in a section intersecting a resilient engagement piece).

On the other hand, as shown in FIG. 19, the resilient engagement pieces 17c of the ring portion 17a biased by the coil spring 16 to be axially moved are axially engaged with the second engagement holes 22 in order to prevent the sleeve 10 from being moved to the proximal side with respect to the syringe barrel 2 to project again to the distal side.

As described above, the syringe according to this embodiment is highly safe because the needle is accommodated before and after the administration. Even without a needle cover adapted to be pressed against a patient's skin to be moved out and in, the syringe can be configured so as to automatically retract the needle by performing the pushing operation for the administration and further performing the pushing operation after the administration. This significantly reduces the possibility of an accident, such as inadvertent injury with the needle during the needle retracting operation.

The present invention is not limited to the aforementioned embodiment. For example, the present invention may be applied to a syringe of a type in which an injection needle is fixed to a distal portion of a syringe barrel by a screw and a plunger extending rearward from the syringe barrel is pushed into the syringe barrel. In this case, the sleeve may be fitted around the syringe barrel, and the coil spring, the spring holder and the like may be provided between the distal portion of the syringe barrel and the distal inner surface of the sleeve.

The components of the syringe may be formed by using proper materials. Preferably, the injection barrel 2 is made of a COP, and the end cap 2b is made of an elastomer or a flexible resin such as an LDPE. Preferably, the gasket 3 is made of an elastomer or a butyl rubber, and the injection needle 5 and the coil spring 16 are made of SUS. Preferably, the needle base 5a is made of a PP, and the stopped 8 is made of a PP. Preferably, the plunger 4, the protection cap 9, the sleeve 10, the flange 10a and the key cylinder 13 are made of a PP or a POM. Preferably, the safety cover 15 is made of a PC, and the spring holder 17 is made of a PP or a POM. Preferably, the plug 50 is made of an elastomer or a butyl rubber, and the plug 50 is covered with a fluororesin.

REFERENCE SIGNS LIST

1: SYRINGE
2: SYRINGE BARREL
3: GASKET
4: PLUNGER
4a: TUBULAR ATTACHMENT PORTION
5: INJECTION NEEDLE
10: SLEEVE
10a: FLANGE
14: MAIN BODY
15: SAFETY COVER
16: COIL SPRING
17: SPRING HOLDER
17a: RING PORTION
17b: LOCK PIECE
17c: RESILIENT ENGAGEMENT PIECE
21: FIRST ENGAGEMENT HOLE
22: SECOND ENGAGEMENT HOLE
50: PLUG

The invention claimed is:

1. A syringe comprising:
a syringe barrel having an inside space to be filled with a liquid drug and an opening at its distal end;
a gasket fitted in the syringe barrel for sealing the liquid drug;
a plunger with a proximal end attached to the gasket and a distal end projecting to a distal side from the opening of the syringe barrel;
an injection needle attached to the plunger, and having a proximal portion to be brought into communication with the inside space at least when the liquid drug is to be administered;
a sleeve axially movable with respect to the injection needle between an administration position such that the injection needle projects from a distal end of the sleeve and an accommodation position such that the injection needle is accommodated in the sleeve, and including a finger hook flange provided on an axially middle portion thereof;
a coil spring provided between the sleeve and the syringe barrel for biasing the sleeve toward the accommodation position;
wherein, when the liquid drug is to be administered, the plunger is axially engaged with the sleeve at the administration position, and the syringe barrel projects from the sleeve to a proximal side;
wherein, by pushing the syringe barrel to a distal side with respect to the sleeve, a volume of the inside space is reduced so that the liquid drug flows out through the injection needle for administration thereof;
wherein, when the sleeve is moved to the accommodation position by a biasing force of the coil spring, the sleeve is axially engaged with the syringe barrel to be locked at the accommodation position,
characterized in that the syringe further comprising a spring holder (17) axially engaging to the sleeve (10) so as to hold the coil spring (16) in a compressed state between the sleeve (10) and the spring holder (17) and to release an engagement by further pushing the syringe barrel (2) distal side after completion of an administration of the liquid drug,
wherein the sleeve (10) is axially movable with respect to the injection needle (5) with the coil spring (16) being held in the compressed state by the spring holder (17) engaging to the sleeve (10).

2. The syringe according to claim 1,
wherein the sleeve includes a cylindrical main body including the finger hook flange, and a safety cover attached to a distal portion of the main body,
wherein the safety cover is engaged with the main body so as to be axially movable with respect to the main body between a compression position and an extension position axially spaced from each other,
wherein the spring holder includes a ring portion provided in opposed relation to the syringe barrel or a distal end of the plunger, and a lock portion to be locked to the safety cover,
wherein the lock portion is connected to the ring portion via a connection portion which is easily breakable,
wherein the coil spring is held in the compressed state between the safety cover and the ring portion,
wherein the main body includes a first engagement recess and a second engagement recess provided in axially spaced relation in an inner surface thereof, the first engagement recess corresponding to the administration position, the second engagement recess corresponding to the accommodation position,
wherein the ring portion has a resilient engagement piece provided on an outer periphery thereof so as to be axially engaged with the first engagement recess of the main body to lock the safety cover at the compression position,
wherein the resilient engagement piece is resiliently deformable radially inward so as to permit movement of the ring portion to the proximal side with respect to the main body,
wherein, when the syringe member is further pushed to the distal side with respect to the sleeve main body after the administration of the liquid drug, the connection portion is broken by a pushing force to release the coil spring,
wherein the ring portion is moved to the proximal side with respect to the main body by the biasing force of the coil spring, and the resilient engagement piece is axially engaged with the second engagement recess, whereby the sleeve and the syringe barrel are axially engaged with each other via the ring portion so as to prevent movement of the sleeve toward the administration position.

3. The syringe according to claim 1, wherein the injection needle is a double ended needle, wherein the injection needle is held in an axially movable manner by the plunger and the sleeve, and is axially spaced away from the gasket to the distal side during the storage before the administration, wherein the plunger includes a tubular attachment portion provided at the proximal end thereof, and the gasket is air-tightly fitted around the tubular attachment portion, wherein a plug is air-tightly fitted in the tubular attachment portion, whereby a sealed aseptic space is defined between the plug and the gasket and the proximal portion of the injection needle penetrates the plug to be located in the sealed aseptic space during the storage.

* * * * *

UNITED STATES PATENT AND TRADEMARK OFFICE
CERTIFICATE OF CORRECTION

PATENT NO. : 9,844,633 B2
APPLICATION NO. : 14/785597
DATED : December 19, 2017
INVENTOR(S) : Yukihiro Ogawa and Yuji Tanaka Page 1 of 1

It is certified that error appears in the above-identified patent and that said Letters Patent is hereby corrected as shown below:

Claim 1, (Column 14, Line 24), after "barrel (2)" insert --to the--.

Signed and Sealed this
Thirtieth Day of January, 2018

Joseph Matal
*Performing the Functions and Duties of the
Under Secretary of Commerce for Intellectual Property and
Director of the United States Patent and Trademark Office*